United States Patent [19]

Panitch

[11] Patent Number: 5,635,165
[45] Date of Patent: Jun. 3, 1997

[54] ANTIPERSPIRANT DEODORANT COMPOSITIONS

[75] Inventor: Maximo M. Panitch, Skokie, Ill.

[73] Assignee: Helene Curtis, Inc., Chicago, Ill.

[21] Appl. No.: 534,277

[22] Filed: Sep. 27, 1995

[51] Int. Cl.$^6$ .............................. A61K 7/32; A61K 7/34; A61K 7/36; A61K 7/38
[52] U.S. Cl. .................. 424/65; 424/66; 424/67; 424/68; 424/400; 424/401; 424/DIG. 5
[58] Field of Search ........................... 424/65, 400, 401, 424/66, 67, DIG. 5, 68

[56] References Cited

U.S. PATENT DOCUMENTS

| | | | |
|---|---|---|---|
| 2,876,163 | 3/1959 | Garizio et al. | 167/90 |
| 3,255,082 | 6/1966 | Barton | 167/90 |
| 3,969,087 | 7/1976 | Saito et al. | 44/7 |
| 4,268,499 | 5/1981 | Keil | 424/68 |
| 4,278,655 | 7/1981 | Elmi | 424/47 |
| 4,350,605 | 9/1982 | Hughett | 252/305 |
| 4,673,570 | 6/1987 | Soldati | 424/66 |
| 4,725,430 | 2/1988 | Schamper et al. | 424/66 |
| 4,780,145 | 10/1988 | Mori et al. | 106/206 |
| 4,822,602 | 4/1989 | Sabatelli | 424/65 |
| 4,853,214 | 8/1989 | Orr | 424/69 |
| 5,013,715 | 5/1991 | Mori et al. | 514/53 |
| 5,019,375 | 5/1991 | Tanner et al. | 424/66 |
| 5,069,897 | 12/1991 | Orr | 424/66 |
| 5,338,534 | 8/1994 | Berndt | 424/69 |

FOREIGN PATENT DOCUMENTS

| | | |
|---|---|---|
| 0440387 | 8/1991 | European Pat. Off. . |
| 0448278 | 9/1991 | European Pat. Off. . |
| 0450597 | 10/1991 | European Pat. Off. . |
| 0512770 | 11/1992 | European Pat. Off. . |
| 0545002 | 6/1993 | European Pat. Off. . |
| 62-121764 | 6/1987 | Japan . |
| 63-143970 | 6/1987 | Japan . |
| 63-143971 | 6/1987 | Japan . |
| 63-260955 | 10/1988 | Japan . |
| 1-203319 | 8/1989 | Japan . |
| 1-207223 | 8/1989 | Japan . |
| 3006283 | 1/1991 | Japan . |
| 2253347 | 9/1992 | United Kingdom . |
| WO93/08840 | 5/1993 | WIPO . |
| WO93/23008 | 11/1993 | WIPO . |
| WO94/24997 | 11/1994 | WIPO . |

OTHER PUBLICATIONS

"Deodorant & Antiperspirant Formulary," *Cosmetics & Toiletries*, vol. 100, Dec., 1985, pp. 65–75.

*Primary Examiner*—Shelley A. Dodson
*Attorney, Agent, or Firm*—Marshall, O'Toole, Gerstein, Murray & Borun

[57] ABSTRACT

Gel antiperspirant compositions comprising an antiperspirant compound, a gelling agent selected from the group consisting of a sterol and a starch hydrolyzate ester of a $C_8$–$C_{22}$ carboxylic acid, a carrier comprising a silicone or a hydrocarbon, and, optionally, a fatty alcohol, a fatty ester, water, or a mixture thereof, are disclosed. Aerosol antiperspirant compositions also are disclosed.

45 Claims, No Drawings

ANTIPERSPIRANT DEODORANT COMPOSITIONS

FIELD OF THE INVENTION

The present invention is directed to anti-perspirant spirant compositions comprising an antiperspirant compound pound, like an astringent salt; a gelling agent selected from the group consisting of a sterol, like lanosterol, a starch hydrolyzate ester of a $C_8$–$C_{22}$ carboxylic acid, like dextrin palmitate, and mixtures thereof; a carrier comprising a silicone or a hydrocarbon; and optionally, water, a fatty alcohol, a fatty ester, or a mixture thereof. The antiperspirant compositions are viscous, gelled compositions that are opaque and phase stable; effectively deliver the antiperspirant compound to the skin; are nonwhitening and nonstaining to skin and clothing after topical application; and exhibit excellent sensory properties. The antiperspirant compositions also can be formulated into aerosol antiperspirant compositions. The present invention also is directed to methods of using the antiperspirant compositions.

BACKGROUND OF THE INVENTION

Antiperspirant compositions are well known in the cosmetic art. An ideal antiperspirant composition is stable for the life of the composition, effectively delivers the antiperspirant compound to the skin, does not leave a visually observable white residue on the skin or clothing, and is esthetically pleasing to the consumer.

Antiperspirant compositions are available in a variety of forms, such as aerosol suspensions; pump sprays; roll-on powders; emulsions, lotions, or suspensions; and solid gels, waxes, creams, or suspensions. Antiperspirant compositions traditionally have been prepared as either oil-in-water emulsions or water-in-oil emulsions. Therefore, antiperspirant compositions of any form typically have a milky or opaque appearance, but some antiperspirant compositions are transparent. Antiperspirant compositions conventionally are manufactured by complex methods. Antiperspirant compositions prepared as emulsions often feel wet or oily when applied to the skin, and often remain tacky after the carrier of the composition evaporates. In addition, many emulsion-type antiperspirant compositions leave a white, staining residue on contacted skin or clothing.

Roll-on and gelled emulsion-type antiperspirant compositions are used by rubbing an area of the body, such as the underarm, to apply a layer of the composition to the skin, and thereby reduce odor and/or perspiration. Roll-on and gel antiperspirant compositions preferably possess the esthetic properties of smoothness, nonoiliness and nontackiness. Gelled antiperspirant compositions also require a sufficient firmness to maintain its shape. Another highly desirable, but hard to achieve, esthetic property is avoiding a visible residue, e.g., a white layer, that is left on the skin or clothing after the antiperspirant composition is applied.

Nonemulsified antiperspirant compositions also are known in the art. However, nonemulsified compositions often require shaking prior to each use in order to redisperse the insoluble antiperspirant compound that has separated from the composition. Nonemulsified antiperspirant compositions that do not require shaking prior to each use, such as an antiperspirant creme or paste, typically include a relatively high percentage of suspending agents, like an organoclay. The presence of an organoclay in an antiperspirant composition is a principal source of the whitening and staining of skin and clothing.

Investigators have searched for antiperspirant compositions that display the above-listed desirable properties. A roll-on antiperspirant is difficult to formulate and manufacture because the composition requires a sufficient viscosity to adhere to the skin, resists dripping off or running down the skin, and yet is not tacky or sticky. A gel antiperspirant composition is difficult to formulate and manufacture because the composition requires sufficient firmness to withstand rubbing across the skin to deliver a sufficient amount of the antiperspirant compound to the skin. Additional formulation parameters include viscosity control, lack of syneresis, and nontackiness.

A gel antiperspirant composition which has esthetic and functional properties equal to or better than presently available antiperspirant compositions is highly desired by consumers. However, providing a commercially acceptable gel antiperspirant composition requires overcoming several formulation and manufacturing problems.

Gelled antiperspirant compositions incorporate a gelling agent to build up the solid structure, or firmness, of the composition. Solid antiperspirant compositions typically are based on solid fatty alcohols containing 14 to 20 carbon atoms as the solidifying agent. In addition, nonvolatile emollients are included in the composition to minimize tackiness and improve sensory properties, thereby improving ease of application, esthetics, and consumer appeal.

Solid antiperspirant compositions are divided into three main classes, i.e., compressed powder sticks, gel sticks and wax sticks. Each of these classes has advantages, but each class also has particular disadvantages. Compressed powder sticks for example are frequently brittle and hard, and leave a cosmetically unacceptable powdery residue after application. Frequently, wax-based products are cosmetically unacceptable because of such factors as hardness, greasiness and tackiness. The visually observable white residue remaining after application also is esthetically undesirable.

Gel-type solid antiperspirant compositions have several advantages over both compressed powder sticks and wax sticks. For example, the gel antiperspirant compositions leave less residue or dust on the skin. The gel antiperspirant compositions also glide easily over the skin surface resulting in an easy and comfortable application of the composition.

However, the preparation of antiperspirant compositions in the form of an effective and stable gel is difficult. For example, a critical ingredient in gel antiperspirant compositions is the gelling agent. Many prior gel antiperspirant compositions contain gelled hydroalcoholic solutions including a gelling agent, such as sodium stearate, to form the gel. However, common gelling agents cannot be used in the presence of acidic antiperspirant compounds because of an interaction between the gelling agent, which is alkaline, and the antiperspirant compound.

Prior gel antiperspirant compositions also typically were divided into three main classes. One of these classes is the optically clear gelled emulsion compositions. These compositions include a water phase and an oil phase. The oil phase is suspended in the water phase by using a sufficient amount of an appropriate emulsifier or emulsifiers. The emulsions conventionally contained waxes, silicones, clays and emollients. The optically clear gelled emulsion compositions are illustrated in U.S. Pat. Nos. 4,673,570, 4,268,499, 4,278,655, and 4,350,605; EP 0 450 597; and in "Deodorant and Antiperspirant Formulary," *Cosmetics & Toiletries*, Dec. 12, 1985, vol. 100, p. 65–75.

The optically clear gelled emulsion compositions often exhibit the disadvantages of composition instability during storage; the development of a hazy or milky appearance during storage; a stringy, tacky, oily consistency and other undesirable esthetics. In additions, the emulsion gel compositions often leave a visible residue, in the form of a white layer, on the skin or clothing. Another disadvantage of optically clear gelled emulsion compositions is the complex method of preparing an optically clear gelled emulsion composition. The method traditionally requires high shear rates during mixing, high processing temperatures, and a series of cooling and heating process steps.

A second class of gel antiperspirant compositions is antiperspirant compositions thickened with 1,3:2,4-dibenzylidene-sorbitol (DBS) or DBS derivatives. Such transparent antiperspirant compositions are disclosed in U.S. Pat. Nos. 4,822,602 and 4,725,430; European Patent Publication 0 512 770; WO91/15191; and WO 92/19222.

Gelled antiperspirant compositions thickened with DBS or DBS-type compounds have a major disadvantage in that the compositions are unstable in the presence of highly acidic antiperspirant compounds at elevated temperatures. In addition, other disadvantages are the high temperature required for manufacturing DBS-thickened compositions (i.e., about 230° F. to about 240° F.), and leaving a visible white residue on the skin and clothing after application.

The third class of gel antiperspirant compositions is the acid-base complex gels. These antiperspirant compositions are prepared by interacting the active antiperspirant compound with a carboxylic acid salt. Acid-based complex gels are disclosed, for example, in U.S. Pat. Nos. 3,255,082 and 2,876,163; and in European Publication No. 0 448 278.

This third class of antiperspirant compositions has a major disadvantage in that the active antiperspirant compound is partially deactivated by the salt, thereby reducing the efficacy of the antiperspirant compound and, accordingly, the antiperspirant composition. In addition, the resulting gels are very brittle, tacky, and/or possess other undesirable esthetic properties, such as in the compositions disclosed in U.S. Pat. No. 3,255,082, which are emulsions or sols.

The problems associated with gel antiperspirants can be partially overcome by formulating a roll-on antiperspirant. Roll-on antiperspirants typically are viscous liquids to semi-solids. However, roll-on antiperspirants often impart a tacky feel and still have the ability to leave an unsightly white residue on the skin. Similarly, aerosol antiperspirants leave a greasy or tacky feeling, or a white residue, on the skin after application.

Investigators have continually sought to provide gel antiperspirant compositions having both long-term stability and sufficient esthetic and functional properties for consumer acceptance. These esthetic and functional properties include a sufficient firmness for application to the skin, no visually observable whitening of the skin and clothing, and the ability to effectively deliver the antiperspirant compound to the skin without providing a tacky or sticky feeling. The present invention is directed to providing gel antiperspirant compositions exhibiting these consumer-acceptable esthetic and functional properties wherein the composition utilizes a nonaqueous carrier and a gelling agent selected from a sterol and a starch hydrolyzate ester of a $C_8$ to $C_{22}$ carboxylic acid. Surprisingly, the compositions can be admixed with a hydrocarbon propellant to provide an aerosol antiperspirant.

Gelled, nonaqueous liquids are known. For example, nonaqueous liquids gelled by the addition of dextrin fatty acid esters are disclosed in Japanese Patent Publications 3,006,283; 1,203,379; 64-207223, 62-121764, 62-143970, and 62-143971. The use of a cellulose fatty acid ester to gel a nonaqueous liquid was disclosed in Japanese Patent Publication 63-360955. A gelling agent for nonaqueous solvent using a combination of a dextrin fatty acid ester and an n-acylaminoacid was disclosed in Japanese Patent Publication 64-207223.

Saito et al. U.S. Pat. No. 3,989,087 and WO93/23008 disclose gelling a nonaqueous system containing aluminum salts using a combination of an n-acylamino-acid amide and 12-hydroxystearic acid. However, high processing temperatures were required to achieve gelling, the product was hard to wash off the skin, and the product lacked consumer-acceptable efficacy. Similar products incorporating polyoxyethylene ether compounds and having improved wash-off properties are disclosed in WO 94/24997. However, the processing temperature required to manufacture the composition offset the improved efficacy.

EP 0,440,387 discloses gelling a $C_1$ to $C_4$ alcohol-based antiperspirant composition with a combination of a hydrophobically-treated clay and sucrose esters of tallow fatty acids. However, the stability of these compositions is low and must be improved to provide a consumer-acceptable antiperspirant composition.

Other patents directed either to gelling agents for non-aqueous compositions or to antiperspirant compositions include UK Patent Application GB 2,253,347, which discloses antiperspirant compositions gelled by a compound having polycyclic aromatic and steroidal groups linked by an ester linkage; Tanner U.S. Pat. No. 5,019,375; Orr U.S. Pat. Nos. 4,853,214 and 5,069,897; European Patent Application Publication No. 0 545 002; and WO 93/08840. Mori et al. U.S. Pat. No. 5,013,715 discloses the use of a fatty acid ester of saccharose to gel a nonaqueous liquid. Mori et al. U.S. Pat. No. 4,780,145 discloses the use of a dextrin fatty acid ester to gel nonaqueous liquids. Berndt U.S. Pat. No. 5,338,535 discloses a talc-free body powder including a starch powder and a volatile silicone.

SUMMARY OF THE INVENTION

The present invention relates to gel antiperspirant compositions having improved efficacy and esthetics, and to methods of using the antiperspirant compositions. The present invention also relates to aerosol antiperspirant compositions. More particularly, the present invention is directed to gel antiperspirant compositions comprising an antiperspirant compound; a gelling agent selected from the group consisting of a sterol, a starch hydrolyzate ester of a $C_8$–$C_{22}$ carboxylic acid, and mixtures thereof; and a carrier comprising a silicone, a hydrocarbon, or a mixture thereof; and optionally, water, a fatty alcohol, a fatty ester, or a mixture thereof.

As used here and hereafter, the term "gel" is defined as a composition that retains its shape in the free form (i.e., is unsupported) at room temperature (i.e., about 25° C.) for at least one hour.

In particular, the gel antiperspirant compositions comprise:

(a) about 1% to about 40% by weight of an antiperspirant compound, like an astringent salt;

(b) about 2% to about 15% by weight of gelling agent selected from the group consisting of a sterol, a starch hydrolyzate ester of a $C_8$–$C_{22}$ carboxylic acid, and mixtures thereof; and (c) about 10% to about 90% by weight of a carrier comprising a silicone, a hydrocarbon, or a mixture thereof.

The gel antiperspirant compositions are free of a particulate filler, like talc, and, therefore, are nonstaining and nonwhitening to skin and clothing. Particulate fillers typically are added to a gel antiperspirant composition to impart firmness to the compositions. Surprisingly, the present antiperspirant compositions have sufficient firmness for product efficacy and consumer esthetics in the absence of a particulate filler. The gelled compositions also effectively deliver the antiperspirant compound to the skin, and exhibit excellent esthetic and functional properties, including sensory properties, for consumer acceptance.

In a preferred embodiment, the gel antiperspirant and deodorant composition comprises:

(a) about 5% to about 35% by weight of an aluminum or zirconium astringent salt, or combination thereof;

(b) about 3% to about 12% by weight of a gelling agent selected from the group consisting of a sterol, a starch hydrolyzate ester of a $C_8$–$C_{22}$ carboxylic acid, and mixtures thereof;

(c) about 15% to about 75% by weight of a carrier selected from the group consisting of a silicone, a hydrocarbon, and mixtures thereof.

In another embodiment, the gel antiperspirant compositions include 0% to about 30% by weight water, 0% to about 20% by weight fatty alcohol, 0% to about 70% by weight fatty ester, or a mixture thereof.

In yet another embodiment, the antiperspirant composition comprising (a), (b), and (c) is admixed with a hydrocarbon propellant to provide an aerosol antiperspirant composition. The aerosol antiperspirant composition contains 1 part by weight gel antiperspirant composition and about 0.5 to about 3 parts by weight of the hydrocarbon propellant.

The present invention also relates to a method of treating or preventing malodors associated with human perspiration, especially underarm odor. The method comprises topically applying an effective amount of a gel antiperspirant composition of the present invention to the skin of a human.

The above and other advantages and novel features of the present invention will become apparent from the following detailed description of the preferred embodiments of the invention.

DETAILED DESCRIPTION OF THE PREFERRED EMBODIMENTS

A gel antiperspirant composition of the present invention comprises an antiperspirant compound, a gelling agent, a carrier, and, optionally, water, a fatty alcohol, a fatty ester, or a mixture thereof. In particular, the gel antiperspirant compositions comprise:

(a) about 1% to about 40% by weight of an antiperspirant compound;

(b) about 2% to about 15% by weight of a gelling agent; and (c) about 10% to about 90% by weight of a carrier comprising a silicone, a hydrocarbon, or a mixture thereof. Optionally, the gelled composition contains 0% to about 30% by weight water; 0% to about 20% by weight fatty alcohol, 0% to about 70% by weight fatty ester, or a mixture thereof. The gel antiperspirant compositions are free of particulate fillers, like talc.

The gel antiperspirant compositions are stable to phase separation and exhibit exceptional esthetic and functional properties. The antiperspirant compositions are firm, nonstringy and nontacky, and are capable of effectively delivering the antiperspirant compound to the skin, without leaving a visually observable white residue on the skin or clothing, i.e., are essentially nonwhitening. The antiperspirant compositions also can be diluted with a hydrocarbon propellant to provide an aerosol antiperspirant composition.

The present gel antiperspirant compositions incorporate any of the antiperspirant compounds known in the art, such as the astringent salts. The astringent salts include organic and inorganic salts of aluminum, zirconium, zinc, and mixtures thereof. The anion of the astringent salt can be, for example, sulfate, chloride, chlorohydroxide, alum, formate, lactate, benzyl sulfonate or phenyl sulfonate. Exemplary classes of antiperspirant astringent salts include aluminum halides, aluminum hydroxyhalides, zirconyl oxyhalides, zirconyl hydroxyhalides, and mixtures thereof.

Exemplary aluminum salts include aluminum chloride and the aluminum hydroxyhalides having the general formula $Al_2(OH)_xQ_y \cdot XH_2O$, wherein Q is chlorine, bromine or iodine; x is about 2 to about 5; x+y is about 6, wherein x and y are not necessarily integers; and X is about 1 to about 6. Exemplary zirconium compounds include zirconium oxy salts and zirconiumhydroxy salts, also referred to as zirconyl salts and zirconyl hydroxy salts, and represented by the general empirical formula $ZrO(OH)_{2-nz}L_z$, wherein z varies from about 0.9 to about 2 and is not necessarily an integer; n is the valence of L; 2−nz is greater than or equal to 0; and L is selected from the group consisting of halides, nitrate, sulfonate, sulfate, and mixtures thereof.

The antiperspirant and deodorant compound is present in the gelled antiperspirant composition in an amount of about 1% to about 40%, and preferably about 5% to about 35%, by weight of the composition. To achieve the full advantage of the present invention, the antiperspirant compound is present in an amount of about 10% to about 30% by weight of the antiperspirant composition.

Examples of antiperspirant compounds include, but are not limited to, aluminum bromohydrate, potassium alum, sodium aluminum chlorohydroxy lactate, aluminum sulfate, aluminum chlorohydrate, aluminum-zirconium tetrachlorohydrate, an aluminum-zirconium polychlorohydrate complexed with glycine, aluminum-zirconium trichlorohydrate, aluminum-zirconium octachlorohydrate, aluminum sesquichlorohydrate, aluminum sesquichlorohydrex PG, aluminum chlorohydrex PEG, aluminum zirconium octachlorohydrex glycine complex, aluminum zirconium pentachlorohydrex glycine complex, aluminum zirconium tetrachlorohydrex glycine complex, aluminum zirconium trichlorohydrex glycine complex, aluminum chlorohydrex PG, zirconium chlorohydrate, aluminum dichlorohydrate, aluminum dichlorohydrex PEG, aluminum dichlorohydrex PG, aluminum sesquichlorohydrex PG, aluminum chloride, aluminum zirconium pentachlorohydrate, and mixtures thereof. Numerous other useful antiperspirant compounds are listed in WO 91/19222 and in the *Cosmetic and Toiletry Fragrance Handbook*, The Cosmetic, Toiletry and Fragrance Association, Inc., Washington, D.C., p. 56, 1989, hereinafter the *CTFA Handbook*, incorporated herein by reference.

Preferred antiperspirant compounds are the aluminum-zirconium chlorides complexed with an amino acid, like glycine, and the aluminum chlorohydrates. Preferred aluminum-zirconium chloride glycine complexes have an aluminum (Al) to zirconium (Zr) ratio of about 1.67 to about 12.5, and a total metal (Al+Zr) to chlorine ratio (metal to chlorine) of about 0.73 to about 1.93.

In addition to the antiperspirant compound, a gel antiperspirant composition of the present invention also includes about 2% to about 15%, and preferably about 3% to about 12%, by weight of the composition, of a gelling agent. To achieve the full advantage of the present invention, the gelling agent is present in an amount of about 3.5% to about 10%, by weight of the composition.

The gelling agent is selected from the group consisting of a starch hydrolyzate ester of a fatty carboxylic acid having about 8 to about 22 carbon atoms (i.e., a $C_8$–$C_{22}$ carboxylic acid), a sterol, and mixtures thereof. The gelling agent acts as a viscosity modifier or thickener to provide an efficacious and consumer-acceptable firmness, and does not contribute to whitening of skin or clothing.

A gel antiperspirant composition including an antiperspirant compound, like an aluminum-zirconium chloride glycine complex, and a gelling agent is a viscous or gelled composition. The viscosity and gel consistency of the composition can be adjusted by the addition of an optional fatty acid ester and/or an optional fatty alcohol to provide a commercially acceptable product.

In one embodiment, the gelling agent comprises a starch hydrolyzate ester of a $C_8$–$C_{22}$ carboxylic acid. These gelling agents are prepared by reacting a starch hydrolyzate with a fatty acid having about 8 to about 22 carbon atoms, under esterifying conditions, to provide a fatty acid esterified with a starch hydrolyzate.

A starch hydrolyzate is a hydrolysis product of starch having the following repeating units:

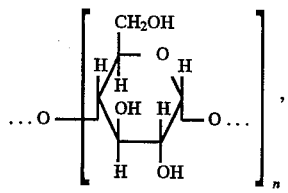
(I)

wherein n is a number from 1 to about 50. A starch hydrolyzate has hydroxyl groups available to esterify a fatty carboxylic acid. The starch hydrolyzates used herein can be linear or cyclic, such as a cyclodextrin.

An exemplary starch hydrolyzate ester of a $C_8$–$C_{22}$ fatty acid is a dextrin fatty acid ester, illustrated in structural formula II:

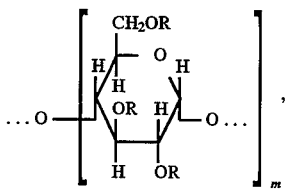
(II)

wherein each R group, individually, is a hydrogen atom or an acyl group having from about 8 to about 22 carbon atoms, provided that at least one R group per glucose unit is an acyl group, and m is an integer from about 20 to about 30. The dextrin fatty acid ester can be a partial ester, i.e., at least one R group is hydrogen; or the dextrin can be completely esterified, i.e., all R groups are a $C_8$–$C_{22}$ acyl group. In preferred embodiments, the degree of substitution wherein the R group is a $C_8$–$C_{22}$ alkyl group is at least 2 (i.e., at least two R groups are $C_8$–$C_{22}$ acyl groups).

The $C_8$–$C_{22}$ fatty acids that are reacted with the starch hydrolyzate can be saturated or unsaturated acids, and include, for example, capric acid, pelargonic acid, caprylic acid, undecylic acid, undecylenic acid, lauric acid, myristic acid, pentadecylic acid, palmitic acid, heptadecylic acid, stearic acid, nonadecanoic acid, arachic acid, oleic acid, linoleic acid, linolenic acid, similar acids, and mixtures thereof. The dextrin fatty acid esters are disclosed in Mori et al. U.S. Pat. No. 4,780,145, incorporated herein by reference, and are available under the tradename RHEOPEARL from Chiba Flour Milling Co., Ltd., Japan. An example of a dextrin fatty acid ester is dextrin palmitate, available commercially as RHEOPEARL KL and RHEOPEARL FL, for example, from Chiba Flour Milling Co., Ltd. Specific, nonlimiting examples of starch hydrolyzate esters of $C_8$–$C_{22}$ carboxylic acids are dextrin behenate, dextrin laurate, dextrin myristate, dextrin palmitate, dextrin stearate, and mixtures thereof.

Another exemplary class of starch hydrolyzate esters of a fatty acid is the sucrose fatty acid esters. Sucrose fatty esters have the structure

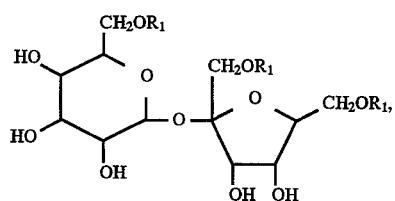

wherein the $R_1$ groups, individually, are a hydrogen atom or an acyl group having about 8 to about 22 carbon atoms, provided that at least one $R_1$ group is an acyl group. Accordingly, one, two, or three of the methylhydroxyl groups (i.e., $CH_2OH$ groups) of sucrose are esterified with a $C_8$–$C_{22}$ fatty acid. Preferred sucrose fatty acid esters have two or three esterified methylhydroxyl groups, i.e., the diester or triester of sucrose. Also contemplated are sucrose derivatives wherein one or more hydrogen atoms of sucrose replaced by an acetyl group, and having at least one $R_1$ group.

Examples of sucrose fatty acid esters include, but are not limited to, sucrose distearate, sucrose cocoate, sucrose dilaurate, sucrose oleate, sucrose palmitate, sucrose polylaurate, sucrose polylinoleate, sucrose polyoleate, sucrose polystearate, sucrose ricinoleate, sucrose stearate, sucrose tribehenate, sucrose tristearate, and mixtures thereof. Sucrose esters are commercially available as the CRODESTA series of sugar esters from Croda Inc., Parsippany, N.J.

More generally, the starch hydrolyzate of a fatty acid ester can be any sugar or carbohydrate ester of a fatty $C_8$–$C_{22}$ carboxylic acid that is capable of gelling a silicone or a hydrocarbon. Other starch hydrolyzates, in addition to sucrose and dextrin, that can be used to esterify a $C_8$–$C_{22}$ carboxylic acid include, but are not limited to, monosaccharides, like glucose, fructose, and mannose; disaccharides, like sucrose, maltose, and lactose; trisaccharides, like maltotriose, raffinose, and melezitose; polysaccharides, like cellulose lose and chitin; and cyclodextrins, like α,β and α-cyclodextrin.

In addition to the starch hydrolyzate fatty acid esters, a sterol can be used as the gelling agent of the present antiperspirant compositions. In particular, sterols are isocyclic compounds having a tetracyclic cyclopentenophenanthrene skeleton (III):

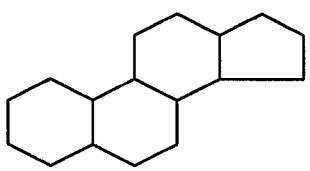
(III)

The sterols can contain hydroxyl or keto groups, ring unsaturation, and methyl or aliphatic side chains. Exemplary, but nonlimiting, sterols include dihydrolanosterol, lanosterol, cholesterol, citosterol, campesterol, cholecalciferol, cholesteryl hydroxystearate, dihydrocholesterol, stigmasterol, β-sitosterol, lanolin alcohol, soy sterol, and tall oil sterol.

Sterols are a major constituent of compounds termed "unsaponifiables." Unsaponifiables are the compounds that remain after saponification of a natural lipid, such as soybean oil. The term "unsaponifiable," therefore, refers to lipid components of natural fats and oils that are not hydrolyzed and remain soluble in lipid solvents after alkaline hydrolysis. Unsaponifiables include hydrocarbons, complex fatty alcohols, and ethers. Sterols, abietyl alcohol, batyl alcohol, and squalene are some of the compounds found in unsaponifiables. Unsaponifiables that can be used as the gelling agent of the present antiperspirant compositions include, but are not limited to, avocado oil unsaponifiables, olive oil unsaponifiables, rapeseed oil unsaponifiables, shea butter unsaponifiables, soybean oil unsaponifiables, and mixtures thereof, or in mixture with a sterol.

Sterols and unsaponifiables are commercially available products, such as NIKKOL® Isocholesterol EX (dihydrolanosterol and lanosterol), Nikko Chemicals Co., Tokyo, Japan, CRODAROM Avocadin (avocado oil unsaponifiables), Croda, Inc., Parsippany, N.J. CRODAROM Avocadin contains β-sitosterol, campesterol, and stigmasterol.

The gel antiperspirant compositions also contain about 10% to about 90%, and preferably about 15% to about 75%, by weight of the composition, of a carrier. To achieve the full advantage of the present invention, the composition includes about 30% to about 60%, by weight, of a carrier.

The carrier is nonaqueous and comprises a volatile silicone, a volatile hydrocarbon, a nonvolatile silicone, a nonvolatile hydrocarbon, or a mixture thereof. Preferably, the carrier comprises a volatile silicone, a volatile hydrocarbon, or a mixture thereof.

In a preferred embodiment, the volatile silicone is a low molecular weight polydimethylsiloxane having a viscosity of about 0.5 to about 5 centistokes (cs) at 25° C. and a boiling point of up to about 300° C. at atmospheric pressure. A low molecular weight polydimethlsiloxane having phenyl substituents also is useful in the compositions of the present invention. Furthermore, the low molecular weight polydimethylsiloxane compound can be a linear or a cyclic polydimethylsiloxane compound.

An example of a linear, low molecular weight, volatile polydimethylsiloxane compound useful in the composition and method of the present invention is hexamethyldisiloxane, available commercially under the tradename DOW CORNING 200 FLUID, from Dow Corning Corp., Midland, Mich. Hexamethyldisiloxane has a viscosity of 0.65 cs (centistokes), is highly volatile, is nongreasy, and does not leave the skin with a sticky or tacky feeling. Other linear polydimethylsiloxanes, such as decamethyltetrasiloxane, having a boiling point of about 195° C. at atmospheric pressure, and a viscosity of 1.5 centistokes; octamethyltrisiloxane; and dodecamethylpentasiloxane, also are useful in the composition of the present invention.

In addition, the cyclic, low molecular weight, volatile polydimethylsiloxanes, having the Cosmetic, Toiletry and Fragrance Association (CTFA) designation cyclomethicone, also are useful in the composition and method of the present invention. The cyclomethicones are low molecular weight, water-insoluble cyclic compounds having an average of about 3 to about 6 —[O—Si(CH₃)₂]—repeating group units per molecule and boil at atmospheric pressure in a range of from about 150° C. to about 250° C. Suitable cyclomethicones are available commercially under the tradenames SILICONE SF-1173 (octamethylcyclotetrasiloxane) and SILICONE SF-1202 (decamethylcyclopentasiloxane) from General Electric, Waterford, N.Y., and SILICONE 344 FLUID and SILICONE 345 FLUID from Dow Corning Corporation, Midland, Mich., the tetramer being listed first in each instance. The volatile cyclic silicones can be used in combination with a linear volatile silicone, and the volatile silicones can be used in conjunction with a nonvolatile silicone or a hydrocarbon.

In addition to the volatile silicones, a volatile hydrocarbon can be included in the composition, either alone or in conjunction with other nonaqueous carriers. The volatile hydrocarbon, such as a hydrocarbon including about 10 carbon atoms to about 26 carbon atoms, has sufficient volatility to avoid leaving a sticky or tacky feeling on the skin. A volatile hydrocarbon, therefore, provides essentially the same benefits as the volatile silicone.

A preferred volatile hydrocarbon is an aliphatic hydrocarbon including from about 12 to about 24 carbon atoms, and has a boiling point in the range of from about 100° C. to about 300° C. Exemplary volatile hydrocarbons are depicted in general structural formula (IV), wherein n ranges from 2 to 5.

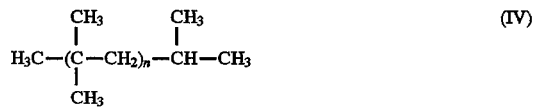
(IV)

Examples of volatile hydrocarbons useful in the compositions of the present invention are the commercially-available compounds such as PERMETHYL 102A, or PERMETHYL 99A and PERMETHYL 101A, corresponding to compound of general structural formula (IV) wherein n is 2 and 3, respectively, from Presperse, Inc., South Plainfield, N.J. Other volatile hydrocarbons include isohexadecene, 1-decene dimer, and C₁₃₋₁₄ isoparaffins. A volatile hydrocarbon is useful in the gel antiperspirant composition either alone, in combination with another volatile or nonvolatile hydrocarbon, or in combination with a volatile or nonvolatile silicone.

In another embodiment, the gel antiperspirant composition contains a carrier comprising a nonvolatile silicone, like a polydimethylsiloxane compound. Preferred nonvolatile silicone compounds include linear and branched polydimethylsiloxanes of the following general formula:

wherein n is a number from 25 to about 200, and preferably from about 50 to about 100. Phenyl-substituted silicones also are useful. Silicone fluids, useful in compositions of the present invention are available from numerous commercial sources, including General Electric Company, Waterford, N.Y., and Dow Corning Corp., Midland, Mich. The nonvolatile polydimethylsiloxane compounds are nonfunctional siloxanes having a viscosity of from about 5 to about 1,000 cs, and preferably from about 25 to about 350 cs, at 25° C.

Another suitable carrier that can be included in the composition of the present invention is a nonvolatile hydrocarbon, such as mineral oil. The nonvolatile hydrocarbons provide many of the same benefits as the silicone conditioning agents, and can be included in the composition in conjunction with a silicone conditioning agent.

In addition to the essential ingredients, the present gel antiperspirant compositions also can include optional ingredients traditionally included in antiperspirant compositions. These optional ingredients include, but are not limited to, dyes, fragrances, preservatives, antioxidants, detackifying agents, deodorizing agents, and similar types of compounds. These optional ingredients typically are included in the antiperspirant composition in an amount of about 0.01% to about 10% by weight of the composition.

In accordance with an important feature of the present invention, the gel antiperspirant composition is free of surfactants and particulate fillers, like talc. The combination of antiperspirant compound, gelling agent, and carrier provides an antiperspirant composition having sufficient firmness to function as a gel, thereby obviating the presence of a particulate filler. The present antiperspirant compositions also are easily and effectively applied to the skin, thereby obviating the presence of a surfactant. The present antiperspirant compositions, therefore, eliminate the unsightly white residue on skin or clothing attributed to the particulate filler.

However, other optional ingredients can be added to the gel antiperspirant composition to improve the composition esthetics for greater consumer acceptance. These optional ingredients include water, a fatty alcohol, a fatty acid ester, or a mixture thereof.

Water can be included in the antiperspirant composition in an amount of 0% to about 30% by weight of the composition, and preferably 0% to about 20% by weight. To achieve the full advantage of the present invention, water is present in an amount of 0% to about 10% by weight of the composition. Water is present in a sufficient amount such that the feel of the composition is not adversely affected, and the composition does not leave a tacky feel on the skin. The addition of water to the composition leads to the formation of a water-in-oil microemulsion, which helps decrease the tacky skin feeling attributed to the water.

Another optional ingredient included in the gel antiperspirant composition can be a fatty alcohol. The fatty alcohol is present in an amount of 0% to about 20%, and preferably 0% to about 15%, by weight of the composi- tion. To achieve the full advantage of the present invention, the fatty alcohol is present at about 1% to about 15% by weight of the composition. The fatty alcohol helps adjust the firmness of the antiperspirant composition to a desired level and increase phase stability. The presence of a fatty alcohol above about 20% by weight provides a composition that is too firm, and, therefore, is difficult to apply to the skin.

The fatty alcohol has about 8 to about 26 carbon atoms, and preferably about 12 to about 22 carbon atoms. The term "about" recognizes that the fatty alcohols often are available as mixtures of alcohols containing predominantly one or two fatty alcohols and minor portions of several other fatty alcohols. Therefore, for example, a commercial fatty alcohol having 8 carbon atoms typically includes alcohols having more than, and less than, 8 carbon atoms. Examples of fatty alcohols include, but are not limited to, lauryl alcohol, oleyl alcohol, myristyl alcohol, tallow alcohol, cetyl alcohol, stearyl alcohol, cetearyl alcohol, caprylic alcohol, $C_{9-11}$ alcohols, $C_{12-13}$ alcohols, $C_{12-15}$ alcohols, $C_{12-16}$ alcohols, $C_{14-15}$ alcohols, coconut alcohol, decyl alcohol, isocetyl alcohol, isostearyl alcohol, palm kernel alcohol, tridecyl alcohol, behenyl alcohol, decyltetradecanol, heptylundecanol, octyldodecanol, undecylenyl alcohol, undecylpentadecanol, and mixtures thereof.

Another optional ingredient is a fatty ester, present in an amount of 0% to about 70%, and preferably 2% to about 50%, by weight of the composition. To achieve the full advantage of the present invention, the fatty ester is present in an amount of about 3% to about 25%, by weight of the composition. The fatty ester is included in the antiperspirant composition as an emollient to improve composition esthetics, especially feel and ease of application.

The fatty ester is a liquid or a solid compound. Preferably, the fatty ester is a liquid compound. The fatty component of the fatty ester can be derived from a fatty acid or a fatty alcohol, or a combination thereof. In addition, the fatty ester can be a straight chain fatty ester, like isopropyl myristate; a branched chain fatty ester, like Purcellin Oil; a benzoate ester, like $C_{12-15}$ alcohols benzoate; or a combination thereof.

One useful class of fatty esters is derived from carboxylic acids having 1 to about 12 carbon atoms, including both branched and straight chain carboxylic acids. In general, the $C_1$ to $C_{12}$ carboxylic acid is esterified with a fatty alcohol including about 8 to about 22 carbon atoms to provide a fatty ($C_8$ to $C_{22}$) ester of a $C_1$ to $C_{12}$ carboxylic acid that is useful in the present invention. Such fatty alcohols include, but are not limited to, lauryl alcohol, myristyl alcohol, cetyl alcohol, cetearyl alcohol, stearyl alcohol, isostearyl alcohol, oleyl alcohol, tallow alcohol, behenyl alcohol, and mixtures thereof. Accordingly, fatty ($C_8$ to $C_{22}$) esters of $C_1$ to $C_{12}$ carboxylic acids useful in the composition and method of the present invention include, but are not limited to, cetyl octanoate, stearyl heptanoate, stearyl caprylate, stearyl octanoate, lauryl octanoate, myristyl heptanoate, oleyl octanoate, myristyl propionate, cetyl acetate, cetyl propionate, cetyl octanoate, isodecyl neopentanoate, and mixtures thereof. These fatty esters can occur naturally or can be synthesized.

In place of, or in combination with, the fatty ($C_8$ to $C_{22}$) ester of a $C_1$ to $C_{12}$ carboxylic acid, a fatty ester derived from a fatty acid including about 8 to about 22 carbon atoms esterified with an alcohol including 1 to about 22 carbon atoms can be included in the composition of the present invention. Examples of such fatty esters include, but are not limited to, isopropyl myristate, isopropyl palmitate, isopropyl laurate, isopropyl linoleate, isopropyl tallowate, isopropyl ricinoleate, methyl laurate, methyl linoleate, methyl myristate, methyl stearate, methyl ricinoleate, methyl carprylate, methyl oleate, methyl palmitate, methyl stearate, methyl behenate, methyl soyate, methyl tallowate, isopropyl behenate, isopropyl isostearate, isopropyl soyate, propyl oleate, butyl oleate, butyl stearate, methyl coconate, methyl lardate, isobutyl palmitate, butyl myristate, ethyl palmitate, ethyl myristate, ethyl oleate, ethyl stearate, isobutyl stearate, isobutyl myristate, and mixtures thereof.

Another class of fatty esters that can be included in the composition of the present invention, either alone or in combination with the fatty esters described above, is the benzoate esters. Suitable benzoate esters include esters of benzoic acid wherein the esterifying alcohol includes about 8 to about 22 carbon atoms. Examples of suitable benzoate esters include, but are not limited to, the commercial products FINSOLV TN, benzoic acid esterified with fatty alcohols including about 12 to about 15 carbon atoms; FINSOLV SB, isostearyl benzoate; FINSOLV P, PPG-15 stearyl ether benzoate; or combinations thereof, all available from Finetex Inc., Elmwood Park, N.J.

Other useful fatty esters are, for example, cetyl stearate, isocetyl stearate, diisopropyl adipate, diiostearyl fumarate, dicetyl adipate, triisostearyl citrate, pentaerythritol tetracocoate, pentaerythritol tetrabehenate, pentaerythritol rosinate, pentaerythritol tetraoctanoate, pentaerythritol tetraisonononoate, pentaerythritol tetraisostearate, pentaerythritol tetralaurate, pentaerythritoltetramyristate, pentaerythritol tetraoleate, pentaerythritol tetrapelargonate, pentaerythritol tetrastearate, pentaerythritol trioleate, and propylene glycol dipelargonate. Additional fatty acid esters are listed in *CFTA Cosmetic Ingredient Handbook, First Edition*, The Cosmetic Toiletry and Fragrance Association, Inc., New York, N.Y. (1988), pp. 23–26, incorporated hereby by reference.

To demonstrate the gel antiperspirant compositions of the present invention, the following nonlimiting examples were prepared. An antiperspirant composition of the present invention is a soft solid gel that leaves no visually-observable, white residue on skin or clothing after application. The antiperspirant compositions also can include, or be diluted with, a hydrocarbon propellant to provide a two-phase aerosol antiperspirant composition.

In general, an antiperspirant composition of the present invention is prepared by first dissolving the gelling agent in the carrier by heating an admixture of the gelling agent and carrier to about 85° C., then maintaining the admixture at 85° C., with agitation, until the mixture is homogeneous. The resulting homogeneous solution is allowed to cool to about 65° C., then the optional fatty alcohol and the optional fatty acid ester, if present, are added to the solution. The resulting mixture is stirred until homogeneous, then the antiperspirant compound and the optional water, if present, are added to the solution, under continued agitation. The resulting antiperspirant composition was stirred at a moderate rate of about 20 to about 100 rpm, then allowed to cool to about 55° C. to about 60° C. until homogeneous. The antiperspirant composition then is cast into a mold, and allowed to cool to room temperature. If other optional oil-soluble components are present in the antiperspirant composition, these components are added to the composition in conjunction with the optional fatty alcohol and fatty ester. If other optional water-soluble components are present in the antiperspirant composition, these components are added to the composition in conjunction with the optional water.

The antiperspirant compositions of the present invention are soft, opaque solid sticks having a penetrometer reading of about 5 to about 40, and preferably about 10 to about 20. The penetrometer reading is determined in accordance with ASTM No. D937-58, "Penetration of Petrolatum." The antiperspirant compositions are sufficiently firm for easy application to the skin without drag. The antiperspirant compositions do not contain a particulate filler, like talc, or a solid inorganic gelling agent, like bentonite, and, therefore, do not leave an esthetically unacceptable white residue on skin or clothing.

As will be demonstrated in the following examples, the antiperspirant compositions were phasestable over the life of the product, were firm (gel), were easy to apply and effectively delivered the antiperspirant compound to the skin, and did not whiten the skin or clothing after application. Each of the following examples was prepared by the above-described method.

EXAMPLE 1

| Ingredient | Weight percent[1] |
| --- | --- |
| Aluminum Chlorohydrate (ACH)[2] | 30 |
| Isopropyl Myristate[3] | 10 |
| Dextrin Palmitate[4] | 10 |
| Cyclomethicone[5] | 50 |

[1] the amount of each ingredient is expressed as % by weight of the total composition, all percents set forth the amount of active ingredient present in the composition;
[2] CHLOROHYDROL Powder, available commercially from Reheis, Inc., Berkeley Heights, New Jersey, as a 100% active material;
[3] optional fatty ester;
[4] RHEOPEARL FL, available commercially from Chiba Flour Milling Co., Ltd., Chiba, Japan, as a 100% active material; and
[5] volatile silicone carrier, DOW CORNING 245 FLUID, available commercially from Dow Corning Corp., Midland, Michigan, as a 100% active material.

The composition of Example 1 was an opaque (i.e., white), soft gel composition which spread easily on the skin and dried quickly, leaving behind an antiperspirant film. In storage stability tests, the composition of Example 1 was phase stable at 80° F. and at 120° F. for at least two months. During the storage tests, no separation of solid antiperspirant compound particles was observed. The composition of Example 1 did not leave a visible white residue on the skin 30 minutes or 120 minutes after application.

Compositions including a relatively low amount of antiperspirant compound, e.g., about 5% to about 15% by weight, are termed deodorants as opposed to antiperspirants. Deodorant compositions also can be made by incorporating a sufficient amount of gelling agent into the composition. An optional fatty alcohol or optional fatty acid ester also can be included to enhance composition esthetics. A sufficient amount of gelling agent, and, if desired optional fatty alcohol and/or fatty acid ester, in the composition provide a gel composition of desired consistency. The amount of gelling agent required to provide the desired composition consistency varies with the identity and the amount of carrier in the composition.

EXAMPLE 2

| Ingredient | Weight percent[1] |
|---|---|
| Aluminum Zirconium Tetrachlorohydrex Gly[6] | 15 |
| C$_{12-15}$ Alkyl Benzoate[7] | 62 |
| Dextrin Palmitate[8] | 8 |
| Mineral Oil[9] | 15 |

[6]REACH AZP-908SUF, available commercially from Reheis, Inc., Berkeley Heights, New Jersey, as a 100% active material
[7]fatty ester, FINSOLV TN, Finetex, Inc., Elmwood Park, New Jersey, as a 100% active material
[8]RHEOPEARL KL, available from Chiba Flour Milling Co., Ltd., Chiba, Japan, as a 100% active material; and
[9]nonvolatile hydrocarbon carrier.

The composition of Example 2 was an opaque, soft solid having a slightly yellowish color. The composition was easily applied to the skin to effectively deliver the antiperspirant compound and was nonwhitening to skin and clothing. The composition was stable for at least two months in accelerated stability tests performed at 80° F. and 120° F.

EXAMPLE 3

| Ingredient | Weight percent[1] |
|---|---|
| Aluminum Chlorohydrate[2] | 30.0 |
| Isopropyl Myristate[3] | 6.0 |
| Dextrin Palmitate[4] | 1.0 |
| Sucrose Distearate[10] | 2.5 |
| Behenyl Alcohol[11] | 10.0 |
| Cyclomethicone[5] | 50.5 |

[10]CRODESTA F-10, available commercially from Croda, Inc., Parsippany, New Jersey, as a 100% active material; and
[11]a C$_{22}$ fatty alcohol, NACOL 22-98, available commercially from Vista Chemical Co., Austin, Texas.

EXAMPLE 4

| Ingredient | Weight percent[1] |
|---|---|
| Aluminum Chlorohydrate[2] | 30 |
| Isopropyl Myristate[3] | 9 |
| Dextrin Palmitate[4] | 10 |
| Water | 5 |
| Cyclomethicone[5] | 46 |

EXAMPLES 5 & 6

| Ingredient | Example 5[1] | Example 6[1] |
|---|---|---|
| Aluminum Chlorohydrate[2] | 30.0 | 30.0 |
| Isopropyl Myristate[3] | 5.7 | 3.4 |
| Dextrin Palmitate[4] | 1.0 | 1.0 |
| Sucrose Distearate[10] | 4.7 | 2.8 |
| Behenyl Alcohol[11] | 9.5 | 5.7 |
| Water | 5.0 | 30.0 |
| Cyclomethicone[5] | 44.1 | 27.1 |

The compositions of Examples 4–6 contained water, and were opaque, soft solid gels having good phase stability and an effective delivery of the antiperspirant composition upon application.

EXAMPLES 7–9

| Ingredient | Example 7[1] | Example 8[1] | Example 9[1] |
|---|---|---|---|
| Aluminum Chlorohydrate[2] | 15 | 30 | 30 |
| C$_{12-15}$ Alkyl Benzoate[7] | 60 | 48 | 25 |
| Isopropyl Myristate[3] | — | — | 5 |
| Dextrin Palmitate[8] | 10 | 10 | 10 |
| Mineral Oil[9] | 15 | 12 | 5 |
| Cycolmethicone[5] | — | — | 25 |

EXAMPLE 10

| Ingredient | Weight percent[1] |
|---|---|
| Aluminum Chlorohydrate[2] | 30 |
| Isopropyl Myristate[3] | 10 |
| Dextrin Palmitate[8] | 10 |
| Isohexadecane[12] | 50 |

[12]volatile hydrocarbon carrier, PERMETHYL 101A, available from Presperse, Inc., South Plainfield, New Jersey, as a 100% active material.

The composition of Example 10, which contains a volatile hydrocarbon carrier, had the same physical characteristics as the composition of Example 1, which contained a volatile silicone carrier. The composition of Example 10 was esthetically acceptable and effectively delivered the antiperspirant compound to the skin.

EXAMPLE 11

| Ingredient | Weight percent[1] |
|---|---|
| Aluminum Zirconium Tetrachlorohydrex Gly[13] | 30 |
| Isopropyl Myristate[3] | 10 |
| Dextrin Palmitate[8] | 2 |
| Sucrose Distearate[10] | 10 |
| Cyclomethicone[5] | 48 |

[13]REACH AZZ-902SUF, available commercially from Reheis, Inc., Berkeley Heights, New Jersey, available as a 100% active material.

EXAMPLES 12–14

| Ingredient | Example 12[1] | Example 13[1] | Example 14[1] |
|---|---|---|---|
| Aluminum Zirconium Trichlorohydrex Gly[14] | 26.5 | 26.5 | — |
| Aluminum Chlorohydrate[2] | — | — | 26.5 |
| Isopropyl Myristate[3] | 6.0 | 6.0 | 6.0 |
| Dextrin Palmitate[8] | 1.0 | 1.0 | 1.0 |
| Sucrose Distearate[10] | 2.5 | 2.5 | 2.5 |
| Behenyl Alcohol[11] | 10.0 | 12.0 | 10.0 |
| Cyclomethicone[5] | 54.0 | 52.0 | 54.0 |

[14]WESTCHLOR ZR30BDMCP, available commercially from Westwood Chemical Corp., Middletown, New York, as a 100% active material.

The compositions of Examples 12–14 were soft solid gels that were stable and performed well as antiperspirant compositions.

EXAMPLE 15

| Ingredient | Weight percent[1] |
|---|---|
| Aluminum Zirconium Trichlorohydrex Gly[14] | 30 |
| Isopropyl Myristate[3] | 10 |

EXAMPLE 15-continued

| Ingredient | Weight percent[1] |
| --- | --- |
| Dihydrolanosterol and Lanosterol[15] | 10 |
| Cyclomethicone[5] | 50 |

[15]NIKKOL® ISOCHOLESTEROL EX, available commericially from Nikko Chemical Co., Ltd., Tokyo, Japan, as a 100% active material containing dihydrolanosterol and lanosterol.

The composition of Example 15 was a soft gel composition that was stable at 80° F. and 120° F. for at least one month. The solid gel composition was sufficiently firm to perform as an antiperspirant composition and effectively delivered the antiperspirant compound to the skin without leaving a tacky or sticky feeling on the skin and without leaving a white residue on the skin or clothing.

EXAMPLE 16

| Ingredient | Weight percent[1] |
| --- | --- |
| Aluminum Zirconium Trichlorohydrex Gly[14] | 26.50 |
| Isopropyl Myristate[3] | 6.00 |
| Dihydrolanosterol and Lanosterol[15] | 1.00 |
| Sucrose Distearate[10] | 1.25 |
| Behenyl Alcohol[11] | 10.00 |
| Cyclomethicone[5] | 55.25 |

EXAMPLE 17

| Ingredient | Weight percent[1] |
| --- | --- |
| Aluminum Zirconium Trichlorohydrex Gly[14] | 26.5 |
| Isopropyl Myristate[3] | 6.0 |
| Avocado Oil Unsaponifiables[16] | 5.0 |
| Behenyl Alcohol[11] | 10.0 |
| Cyclomethicone[5] | 52.5 |

[16]CRODAROM AVOCADIN, available commercially from Croda, Inc., Parsippany, New Jersey, as a 100% active material.

The compositions of Examples 16 and 17 were white, solid vanishing creams having a stability of at least one month at 80° F. and at 120° F. The compositions of Examples 16 and 17 effectively delivered the antiperspirant compound to the skin.

As stated above, one part by weight of the gel antiperspirant compositions can be admixed with about 0.5 to about 3 parts by weight of a hydrocarbon propellant to provide an aerosol antiperspirant composition. Aerosol antiperspirant compositions are illustrated in Examples 18 and 19.

EXAMPLES 18–19

| Ingredient | Example 18[1] | Example 19[1] |
| --- | --- | --- |
| Aluminum Chlorohydrate[2] | 10.0 | 10.00 |
| Isopropyl Myristate[3] | 2.5 | 2.50 |
| Dextrin Palmitate[4] | 1.0 | 0.50 |
| Sucrose Distearate[10] | 2.5 | 1.25 |
| Cyclomethicone[5] | 24.0 | 25.75 |
| Propellant Blend[17] | 60.0 | 60.00 |

[17]hydrocarbon propellant blend containing about 61% n-butane, about 22% isobutane, and about 16% propane, by weight.

The aerosol compositions of Examples 18 and 19 were two-phase compositions that effectively dispersed the pressurized antiperspirant composition. The aerosol antiperspirant composition was soft and nongreasy. A slight white residue was observed immediately after the aerosol composition was applied to the skin, but the white residue vanished with one to five minutes.

As illustrated by the above examples, the antiperspirant compositions of the present invention have excellent esthetic and functional properties, such as delivery, viscosity, firmness, and low tack. The compositions have an excellent stability at room temperature and at elevated temperatures.

The antiperspirant compositions of the present invention exhibited excellent sensory properties upon topical application to skin. The improved physical and sensory properties include a consistency to effectively deliver the antiperspirant compound to the skin, storage stability, and essentially no whitening of the skin and clothing after topical application.

It should be understood that the foregoing detailed description is given merely by way of illustration. Obviously, many modifications and variations of the invention as hereinbefore set forth can be made without departing from the spirit and scope thereof, and, therefore, only such limitations should be imposed as are indicated by the appended claims.

What is claimed is:

1. A gel antiperspirant composition comprising:

(a) about 1% to about 40% by weight of an antiperspirant compound, wherein the antiperspirant compound is an astringent salt comprising aluminum, zirconium, zinc, or a mixture thereof;

(b) about 2% to about 15% by weight of a gelling agent consisting essentially of a starch hydrolyzate ester of a carboxylic acid having about 8 to about 22 carbon atoms; and (c) about 10% to about 90% by weight of a carrier comprising a silicone, a hydrocarbon, or a mixture thereof.

2. The antiperspirant composition of claim 1 further comprising 0% to about 30% by weight water.

3. The antiperspirant composition of claim 1 further comprising 0% to about 20% by weight of a fatty alcohol having about 8 to about 26 carbon atoms.

4. The antiperspirant composition of claim 1 further comprising 0% to about 70% by weight of a fatty ester.

5. The antiperspirant composition of claim 1 further comprising 0% to about 30% by weight water, 0% to about 20% by weight of a fatty alcohol having about 8 to about 26 carbon atoms, 0% to about 70% by weight of a fatty ester, and mixtures thereof.

6. The antiperspirant composition of claim 1 having a penetrometer reading of about 5 to about 40.

7. The antiperspirant composition of claim 1 wherein the antiperspirant compound is selected from the group consisting of aluminum chlorohydrate, aluminum-zirconium tetrachlorohydrate, an aluminum-zirconium polychlorohydrate complexed with glycine, aluminum-zirconium trichlorohydrate, aluminum-zirconium octachlorohydrate, aluminum sesquichlorohydrate, aluminum sesquichlorohydrex PG, aluminum chlorohydrex PEG, aluminum zirconium octachlorohydrex glycine complex, aluminum zirconium pentachlorohydrex glycine complex, aluminum zirconium tetrachlorohydrex glycine complex, aluminum zirconium trichlorohydrex glycine complex, aluminum chlorohydrex PG, zirconium chlorohydrate, aluminum dichlorohydrate, aluminum dichlorohydrex PEG, aluminum dichlorohydrex PG, aluminum sesquichlorohydrex PG, aluminum chloride, aluminum zirconium pentachlorohydrate, and mixtures thereof.

8. The antiperspirant composition of claim 1 wherein the starch hydrolyzate ester comprises a dextrin fatty acid ester acid having the formula

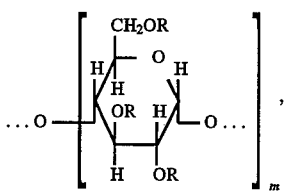

wherein R, individually, is a hydrogen atom or an acyl group having about 8 to about 22 carbon atoms, provided that at least one R group per repeating unit is an acyl group, and m is an integer from about 20 to about 30.

9. The antiperspirant composition of claim 8 wherein at least two R groups are an acyl group having about 8 to about 22 carbon atoms.

10. The antiperspirant composition of claim 8 wherein the acyl group having about 8 to about 22 carbon atoms is derived from capric acid, pelargonic acid, caprylic acid, undecylic acid, undecylenic acid, lauric acid, myristic acid, pentadecylic acid, palmitic acid, heptadecylic acid, stearic acid, nonadecanoic acid, arachic acid, oleic acid, linoleic acid, linolenic acid, or mixtures thereof.

11. The antiperspirant composition of claim 8 wherein the dextrin fatty acid ester comprises dextrin benenate, dextrin laurate, dextrin myristate, dextrin palmitate, dextrin stearate, or mixtures thereof.

12. The antiperspirant composition of claim 1 wherein the starch hydrolyzate ester comprises a sucrose fatty acid ester having the structure

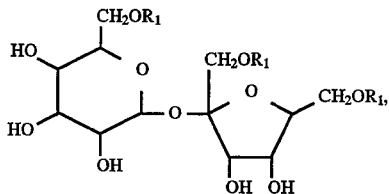

wherein $R_1$, individually, is a hydrogen atom or an acyl group having about 8 to about 22 carbon atoms, provided that at least one $R_1$ group is an acyl group.

13. The antiperspirant composition of claim 12 wherein at least two $R_1$ groups are acyl groups having about 8 to about 22 carbon atoms.

14. The antiperspirant composition of claim 12 wherein the sucrose fatty acid ester comprises sucrose distearate, sucrose cocoate, sucrose dilaurate, sucrose oleate, sucrose palmitate, sucrose polylaurate, sucrose polylinoleate, sucrose polyoleate, sucrose polystearate, sucrose ricinoleate, sucrose stearate, sucrose tribehenate, sucrose tristearate, or mixtures thereof.

15. The antiperspirant composition of claim 1 wherein the starch hydrolyzate is selected from the group consisting of a monosaccharide, a disaccharide, a trisaccharide, a polysaccharlde, a cyclodextrin, and mixtures thereof.

16. The antiperspirant composition of claim 1 wherein the starch hydrolyzate is selected from the group consisting of an α-cyclodextrin, β-cyclodextrin, δ-cyclodextrin, glucose, fructose, mannose, sucrose, maltose, lactose, maltotriose, raffinose, melezitose, cellulose, chitin, and mixtures thereof.

17. The antiperspirant composition of claim 1 wherein the carrier comprises a volatile silicone compound.

18. The antiperspirant composition of claim 17 wherein the volatile silicone compound is a linear volatile silicone having methyl groups, phenyl groups, or a mixture thereof, a viscosity of about 0.5 to about 5 centistokes, and a boiling point of up to about 300° C at atmospheric pressure.

19. The antiperspirant composition of claim 17 wherein the volatile silicone compound is a cyclic volatile silicone having an average of about 3 to about 6 —[O—Si(CH$_3$)$_2$]— repeating group units per molecule and a boiling point at atmospheric pressure in a range of about 150° C. to about 250° C.

20. The antiperspirant composition of claim 1 wherein the carrier comprises a volatile hydrocarbon compound.

21. The antiperspirant composition of claim 20 wherein the volatile hydrocarbon compound has about 10 to about 26 carbon atoms and a boiling point at atmospheric pressure of about 100° C. to about 300° C.

22. The antiperspirant composition of claim 20 wherein the volatile hydrocarbon compound as the structure

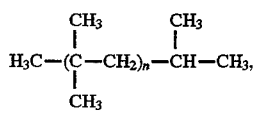

wherein n ranges from 2 to 5.

23. The antiperspirant composition of claim 19 wherein the volatile hydrocarbon compound comprises isohexadecene, 1-decene dimer, a $C_{13-14}$ isoparaffin, or a mixture thereof.

24. The antiperspirant composition of claim 1 wherein the carrier comprises a nonvolatile hydrocarbon, a nonvolatile silicone, or a mixture thereof.

25. The antiperspirant composition of claim 24 wherein the nonvolatile silicone comprises a polydimethylsiloxane compound, and the nonvolatile hydrocarbon comprises mineral oil.

26. The antiperspirant composition of claim 3 wherein the fatty alcohol is present in an amount of about 1% to about 15% by weight of the composition.

27. The antiperspirant composition of claim 3 wherein the fatty alcohol is selected from the group consisting of lauryl alcohol, oleyl alcohol, myristyl alcohol, tallow alcohol, cetyl alcohol, stearyl alcohol, cetearyl alcohol, caprylic alcohol, a $C_{9-11}$ alcohol, a $C_{12-13}$ alcohol, a $C_{12-15}$ alcohol, a $C_{12-16}$ alcohol, a $C_{14-5}$ alcohol, decyl alcohol, isocetyl alcohol, isostearyl alcohol, palm kernel alcohol, tridecyl alcohol, behenyl alcohol, decyltetradecanol, heptylundecanol, octyldodecanol, undecylenyl alcohol, undecylpentadecanol, and mixtures thereof.

28. The antiperspirant composition of claim 4 wherein the fatty ester is present in an amount of about 3% to about 25% by weight of the composition.

29. The antiperspirant composition of claim 4 wherein the fatty ester is derived from a carboxylic acid having 1 to about 12 carbon atoms and an alcohol having about 8 to about 22 carbon atoms.

30. The antiperspirant composition of claim 4 wherein the fatty ester is derived from a carboxylic acid having about 8 to about 22 carbon atoms and an alcohol having about 1 to about 22 carbon atoms.

31. The antiperspirant composition of claim 4 wherein the fatty ester comprises benzoic acid esterified with an alcohol having about 8 to about 22 carbon atoms.

32. The antiperspirant composition of claim 4 wherein the fatty ester is selected from the group consisting of cetyl stearate, isocetyl stearate, diisopropyl adipate, diiostearyl fumarate, dicetyl adipate, triisostearyl citrate, pentaerythritol tetracocoate, pentaerythritol tetrabehenate, pentaerythritol rosinate, pentaerythritol tetraoctanoate, propylene glycol dipelargonate, and mixtures thereof.

33. The antiperspirant composition of claim 1 wherein the composition is free of a particulate filler.

34. A gel antiperspirant composition comprising:
(a) about 5% to about 35% by weight of an aluminum halide, an aluminum hydroxyhalide, a zirconyl oxyhalide, a zirconyl hydroxyhalide, an aluminum zirconium glycinate, or a mixture thereof;
(b) about 3% to about 12% by weight of a gelling agent selected from the group consisting of a sucrose distearate, dextrin palmitate, and mixtures thereof; and
(c) about 15% to about 75% by weight of a carrier selected from the group consisting of a volatile silicone, a volatile hydrocarbon, and mixtures thereof.

35. The antiperspirant composition of claim 34 further comprising 0% to about 20% by weight water, 0% to about 15% by weight of a fatty alcohol selected from the group consisting of behenyl alcohol and stearyl alcohol, and 2% to about 50% by weight of a fatty ester selected from the group consisting of isopropyl myristate, a $C_{12-15}$ alkyl benzoate, and mixtures thereof.

36. An aerosol antiperspirant composition comprising:
(a) 1 part by weight of the gel antiperspirant composition of claim 1, and
(b) about 0.5 to about 3 parts by weight of a hydrocarbon propellant.

37. A method of treating or preventing malodors associated with human perspiration comprising topically applying an effective amount of an antiperspirant composition to human skin, said composition comprising:
(a) about 1% to about 40% by weight of an antiperspirant compound, wherein the antiperspirant compound is an astringent salt comprising aluminum, zirconium, zinc, or a mixture thereof;
(b) about 2% to about 15% by weight of a gelling agent consisting essentially of a starch hydrolyzate ester of a carboxylic acid having about 8 to about 22 carbon atoms; and
(c) about 10% to about 90% by weight of a carrier comprising a silicone, a hydrocarbon, or a mixture thereof.

38. The method of claim 36 wherein the human skin having the antiperspirant composition applied thereon as no visually observable white residue.

39. A gel antiperspirant composition comprising:
(a) about 1% to about 40% by weight of an antiperspirant compound, wherein the antiperspirant compound is an astringent salt comprising aluminum, zirconium, zinc, or a mixture thereof;
(b) about 2% to about 15% by weight of a gelling agent selected from the group consisting of a sterol; and
(c) about 10% to about 90% by weight of a carrier comprising a silicone, a hydrocarbon, or a mixture thereof.

40. The antiperspirant composition of claim 39 further comprising 0% to about 30% by weight water, 0% to about 20% by weight of a fatty alcohol having about 8 to about 26 carbon atoms, 0% to about 70% by weight of a fatty ester, and mixtures thereof.

41. The antiperspirant composition of claim 39 wherein the composition is free of a particulate filler.

42. A gel antiperspirant composition comprising:
(a) about 5% to about 35% by weight of an aluminum halide, an aluminum hydroxyhalide, a zirconyl oxyhalide, a zirconyl hydroxyhalide, an aluminum zirconium glycinate, or a mixture thereof;
(b) about 3% to about 12% by weight of a gelling agent selected from the group consisting of dihydrolanosterol, lanosterol, avocado oil unsaponifiables, and mixtures thereof; and
(c) about 15% to about 75% by weight of a carrier selected from the group consisting of a volatile silicone, a volatile hydrocarbon, and mixtures thereof.

43. The antiperspirant composition of claim 34 further comprising 0% to about 20% by weight water, 0% to about 15% by weight of a fatty alcohol selected from the group consisting of behenyl alcohol and stearyl alcohol, and 2% to about 50% by weight of a fatty ester selected from the group consisting of isopropyl myristate, a $C_{12-15}$ alkyl benzoate, and mixtures thereof.

44. An aerosol antiperspirant composition comprising:
(a) 1 part by weight of the gel antiperspirant composition of claim 43, and
(b) about 0.5 to about 3 parts by weight of a hydrocarbon propellant.

45. The antiperspirant composition of claim 39 wherein the sterol comprises dihydrolanosterol, lanosterol, cholesterol, citosterol, campesterol, cholecalciferol, cholesteryl hydroxystearate, dihydrocholesterol, stigmasterol, β-sitosterol, lanolin alcohol, soy sterol, tall oil sterol, avocado oil unsaponifiables, olive oil unsaponifiables, rapeseed oil unsaponifiables, shea butter unsaponifiables, soybean oil unsaponifiables, or mixtures thereof.

* * * * *